(12) United States Patent
Lindner

(10) Patent No.: US 9,121,765 B2
(45) Date of Patent: Sep. 1, 2015

(54) METHOD AND DEVICE FOR INSPECTING CONTAINERS AND PREFORMS

(75) Inventor: Peter Lindner, Langquaid (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 14/343,012

(22) PCT Filed: Jul. 11, 2012

(86) PCT No.: PCT/EP2012/063565
§ 371 (c)(1),
(2), (4) Date: Apr. 11, 2014

(87) PCT Pub. No.: WO2013/041260
PCT Pub. Date: Mar. 28, 2013

(65) Prior Publication Data
US 2014/0240699 A1    Aug. 28, 2014

(30) Foreign Application Priority Data
Sep. 20, 2011  (DE) .......................... 10 2011 083 037

(51) Int. Cl.
*G01N 21/00* (2006.01)
*G01J 1/42* (2006.01)
*B07C 5/34* (2006.01)
*G01N 21/90* (2006.01)

(52) U.S. Cl.
CPC .................. *G01J 1/42* (2013.01); *B07C 5/3408* (2013.01); *G01N 21/90* (2013.01); *G01N 21/9072* (2013.01); *G01N 21/9081* (2013.01)

(58) Field of Classification Search
CPC .............. G01N 21/90; G01N 21/9036; G01N 21/9018; G01N 21/9027; G01N 21/9081; G01N 2021/8822; G01N 2021/8832; G01N 2021/887; G01N 2021/8887; G01N 2021/9511; G01N 2021/9583; G01N 21/9072; G01N 21/958
See application file for complete search history.

(56) References Cited

U.S. PATENT DOCUMENTS

| 3,218,463 A | 11/1965 | Calhoun |
| 4,586,080 A * | 4/1986 | Hoyt et al. ..................... 348/133 |
| 5,558,836 A | 9/1996 | Rounbehler et al. |
| 6,239,870 B1 * | 5/2001 | Heuft .......................... 356/239.5 |
| 2005/0248766 A1 * | 11/2005 | Niedermeier et al. ........ 356/428 |

(Continued)

FOREIGN PATENT DOCUMENTS

| DE | 4126885 A1 | 2/1993 |
| DE | 19741384 A1 | 3/1999 |

(Continued)

OTHER PUBLICATIONS

International PCT Search Report for PCT/EP2012/063565, dated Sep. 13, 2012.

(Continued)

*Primary Examiner* — Michael P Stafira
(74) *Attorney, Agent, or Firm* — Marshall, Gerstein & Borun LLP

(57) ABSTRACT

A method and a device for inspecting containers and/or preforms. A scattering medium is provided in the interior of the containers or preforms and is irradiated in such manner that the scattering medium forms a bright field behind the container or preform wall area to be imaged. In this way, the wall area can easily be illuminated and imaged from different directions, so that inspection units can be created with a high degree of design freedom and with smaller dimensions.

18 Claims, 1 Drawing Sheet

(56) References Cited

U.S. PATENT DOCUMENTS

| | | | |
|---|---|---|---|
| 2006/0072111 A1* | 4/2006 | Budd et al. | 356/427 |
| 2008/0291438 A1* | 11/2008 | Akkerman et al. | 356/240.1 |
| 2009/0002700 A1* | 1/2009 | Wang et al. | 356/301 |
| 2013/0271755 A1* | 10/2013 | Lindner | 356/240.1 |

FOREIGN PATENT DOCUMENTS

| | | |
|---|---|---|
| DE | 10310273 A1 | 9/2004 |
| DE | 102004062661 A1 | 7/2006 |
| DE | 10164058 B4 | 6/2008 |
| DE | 60315138 T3 | 7/2011 |
| EP | 0663069 B1 | 11/2005 |
| WO | WO-01/25761 A1 | 4/2001 |
| WO | WO-2007/045235 A1 | 4/2007 |
| WO | WO-2010/012631 A1 | 2/2010 |

OTHER PUBLICATIONS

German Search Report for DE 10 2011 083 037.5, dated Jan. 12, 2012.

* cited by examiner

METHOD AND DEVICE FOR INSPECTING CONTAINERS AND PREFORMS

CROSS-REFERENCE TO RELATED APPLICATION

The present application is the US national phase of International Patent Application No. PCT/EP2012/063565, filed Jul. 11, 2012, which application claims priority to German Application No. 10 2011 083 037.5, filed Sep. 20, 2011. The priority application, DE 10 2011 083 037.5, is hereby incorporated by reference.

FIELD OF THE DISCLOSURE

The present disclosure relates to a method and a device for inspecting containers and/or preforms.

BACKGROUND

Containers, such as for example, beverage bottles, are normally examined for the presence of damage and/or foreign particles prior to the filling of the product. It is known, for example, from EP 0663069 B1 to image the side wall of empty bottles in bright field from multiple circumferential directions using a camera and a mirror cabinet. Due to light refraction at the curved boundary surfaces between the bottle wall and the air, however, it is necessary for purposes of exposure to use comparatively wide surface-emitting lamps, which causes an undesirably excessive need for space. Moreover, surface-emitting lamps and cameras for the sidewall inspection must be arranged opposite one another transverse to the transport direction. In order to image containers in their entirety, at least two such inspection units must then be provided, one behind the other. In favor of an optionally compact design of the inspection units, the containers are also rotated about their main axis between the former. This results in additional complexity.

In other inspection units, such as for inspecting the bottom of empty bottles, the problem occurs that in the case of irregular shapes, such as for example behind recessed grips, a directional bright field irradiation of each wall area is hampered or, in part, impossible. Where wall areas to be inspected are shaded, reliable inspection of the empty bottles is impossible or possible only to a limited extent.

There is a need therefore for alternative methods of inspection and inspection devices in which the aforementioned problems do not occur, or occur in only a milder form.

SUMMARY OF THE DISCLOSURE

Accordingly, the following steps are provided:
a) providing a scattering medium in the interior of the containers or preforms;
b) irradiating the scattering medium in such a way that the scattering medium forms a bright field behind a wall area of the container or preform to be imaged; and
c) imaging the wall area.

The irradiated scattering medium therefore provides a virtual diffuse light source. As a result it is possible to arrange radiation sources for irradiating the scattering medium outside the image area of the camera. It is possible, for example, to align the main beam direction of the radiation source essentially orthogonally to the optical axis of the imaging object. This allows comparatively compact inspection units to be implemented.

The scattering medium in step c) is preferably present in gaseous form, in particular in the form of steam, mist and/or smoke. This allows the scattering medium to be distributed comparatively easily and uniformly in the interior of the container or preform. This makes possible a comparatively homogenous virtual light source for generating the bright field. In addition, gaseous fluids can also be introduced at high speed into the container. Moreover, filling plants are able with fluids to comply with hygienic standards.

Preferably, the scattering medium is heavier than air. This simplifies the handling of the container or preform in which the scattering medium is admitted. The scattering medium could then continue to remain in the container for a subsequent treatment step, for example, an aseptic cold filling. When using lighter scattering mediums, the mouth of the container may also be temporarily sealed, depending on need.

In a particularly advantageous embodiment, the scattering medium is supplied in cooled liquid phase, in particular in the form of liquid nitrogen. It is then possible to produce a scattering mist in a simple manner, in particular in combination with natural or artificially produced atmospheric moisture. In this case, nitrogen has the advantage that it can continue to remain in the containers, for example, for a subsequent aseptic cold filling. The nitrogen may be dosed, for example, within 10 milliseconds, in particular with 5 milliseconds.

The scattering medium preferably comprises a pressure-release mist, in particular a mist resulting from a release of pressure during manufacture of the container. Suitable pressure-release mists are formed upon interaction of oxygen with air moisture during the abrupt discharge when demolding blown plastic containers, for example, PET bottles. Thus, during manufacture of the containers, it is possible to use release mist accruing as a waste product as a scattering medium according to the invention. If necessary, such manufacturing-related release mists may also be supplemented in the area of the inspection unit by other and/or similar scattering mediums.

Preferably, the scattering medium in step c) is in contact with the wall area. In this way the wall areas to be inspected may be illuminated uniformly and free of shading. Thus, all of the wall areas to be inspected may be diffusely backlit with the bright field according to the invention. In the case of a directional bright field irradiation on the other hand, dark zones possibly caused by light refraction are formed, in which an empty bottle inspection is impossible or possible but only with insufficient reliability. The scattering medium may be uniformly distributed, for example by swirling, in a suitable manner within the container or preform to be inspected.

The scattering medium preferably has a sterilizing effect. In particular, this facilitates a subsequent filling at low temperatures. If applicable, this can save an additional treatment step involving disinfecting.

In a particularly advantageous embodiment of the method according to the present disclosure, the wall area to be imaged is the bottom of the container or preform, and the scattering medium is irradiated through the side wall and/or the mouth of the container or preform. With the aid of the scattering medium it is possible, in particular through the side wall, if necessary however, also through the narrow mouth of the container, to illuminate all areas of the container bottom. In particular, shading resulting from indentations, such as recessed grips and the like, may be avoided.

In a further advantageous embodiment of the method according to the present disclosure, the wall area to be imaged is the side wall of the container or preform, and the scattering medium is irradiated from above and/or from below, in particular through the mouth and/or the bottom of the container or preform. Thus, it is possible to carry out irradiation that is oriented essentially parallel to the main axis of the container. This allows for a rotationally symmetrical illumination of the container or preform from the inside. A bright field can therefore be generated which can essentially be simultaneously viewed and imaged from all circumferential viewing directions. In other words, the radiation sources may be arranged completely circumferentially outside the image area of the camera, thereby enabling a circumferentially complete sidewall inspection in one single inspection position. In particular, lateral wall areas disposed opposite one another may be imaged virtually simultaneously by means of suitably arranged cameras and the irradiation according to the invention, i.e. in immediately consecutive camera images. In such case, irradiation of the scattering medium on both sides through the container mouth and container bottom allows a particularly uniform bright field to be produced.

Preferably, the spatial distribution of the scattering medium in the area of the wall segment to be imaged is essentially symmetrical relative to the main axis of the container. In this way a bright field can be provided which is viewable from all lateral camera positions regardless of the rotational position of the container. This simplifies in particular the bright field illumination for the side wall inspection of empty bottles or preforms. The scattering medium may diffuse automatically in the container in a suitable manner or may be swirled in order to achieve as homogenous a distribution as possible.

In a preferred embodiment of the method according to the present disclosure, the containers or preforms in the steps a) to c) are moved along a conveyor line. This allows the method to be advantageously employed in a continuous flow of products to be inspected.

Preferably, the scattering medium is irradiated from at least two different main radiation directions in succession in order to provide at least two bright fields along the conveyor line for inspecting different wall areas. In other words, the scattering medium in the containers or preforms may be used for varying inspections. Thus, the scattering medium may remain in the containers or preforms to be inspected, so that only the direction from which the scattering medium is irradiated need be changed. This allows the number and/or dimensions of the light sources required for producing the different bright fields to be reduced.

In a particular embodiment, the device comprises at least one camera for imaging a wall area of the containers or preforms to be inspected, a means for providing and/or distributing a scattering medium in the interior of the containers or preforms, and at least one radiation source for illuminating the scattering medium in such a way that the illuminated scattering medium forms a bright field during imaging of the wall area. The scattering medium is preferably introduced with a metering device, for example, as cooled liquid phase. This enables a suitable scattering medium to be provided in a simple manner, in particular in combination with prevailing air moisture. The scattering medium may be introduced in liquid phase in the container or preform within a few milliseconds, whereupon a suitable scattering mist forms in the interior of the container or preform. The scattering medium may, however, also be produced outside the device according to the invention, for example, as a result of pressure-release during the demolding of blown containers.

Preferably, the main radiation direction of the radiation source and the viewing direction of the camera differ from one another by 45° to 135° relative to the main axis of the container or preform. This enhances the freedom of design and reduces the space requirement, provided that neither the radiation source nor the camera are allowed to collide with the transport line. This also allows for circumferentially complete imaging of the container or preform to be inspected in the area of a radiation source.

In one particularly advantageous embodiment, at least two cameras are provided opposite one another on both sides of a transport line for the containers or preforms in the area of the radiation source, such that the cameras are, at a common inspection point relative to the transport line and/or simultaneously, able to image the irradiated containers or preforms. This allows opposing side wall areas of the containers or preforms to be inspected without changing their rotational position in relation to the transport line. Particularly compact inspection units may be realized as a result. In particular, changing the rotational position between two separate inspection units for purposes of side wall inspection becomes unnecessary.

BRIEF DESCRIPTION OF THE SEVERAL VIEWS OF THE DRAWINGS

A preferred embodiment of the present disclosure is described in the drawing, in which.

DETAILED DESCRIPTION OF THE PREFERRED EMBODIMENTS

Figure 1:
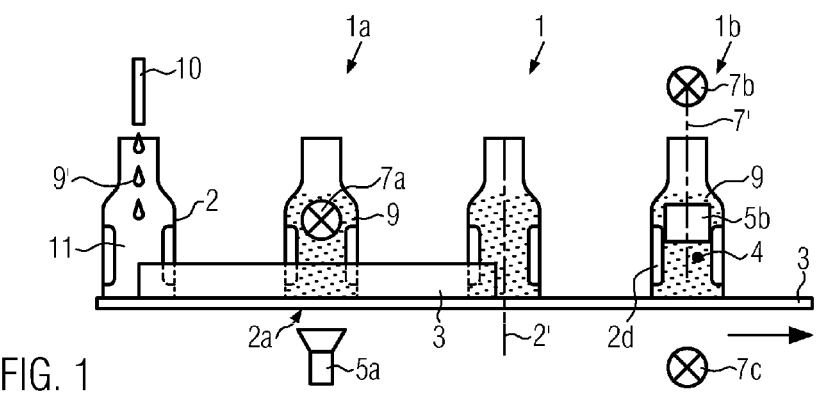
FIG. 1 is a schematic side view of a preferred embodiment of the inspection device according to the present disclosure.

As is apparent from FIG. 1, the device 1 according to the present disclosure is preferably used to inspect empty containers 2 which may, for example, consist of plastic or glass, in particular for detecting foreign particles 4, damage and the like. The inspection device 1 comprises, for example, a first inspection unit 1a for inspecting the bottom of the containers 2 and a second inspection unit 1b for inspecting the side walls of the containers 2. The inspection device 1 is located in the area of a transporter 3, which may be designed, for example, as a linear or carousel-shaped transport line.

Figure 2:
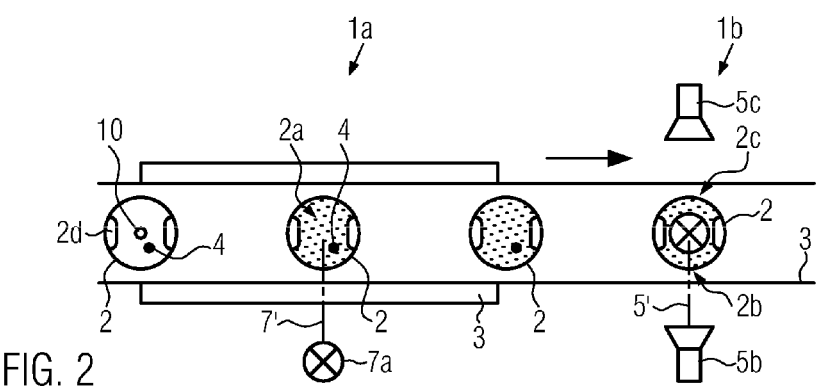
FIG. 2 is a schematic top view of the inspection device of FIG. 1.

According to FIGS. 1 and 2 cameras 5a to 5c are also provided as well as radiation sources 7a to 7c, which may be pulsed light diodes, for example, or flash lamps and the like. A scattering medium 9 is provided in the containers 2, for example, in the form of a mist. The scattering medium 9 is illuminated by each of the radiation sources 7a to 7c in order with the scattering medium 9 to produce a diffuse bright field, which then illuminates in transmitted light the wall area 2a to 2c of the containers 2 to be imaged by each of cameras 5a to 5c.

The scattering medium 9 is distributed in the interior of the containers 2 in such a way that the wall areas 2a to 2c of the containers 2 to be inspected are in contact with the scattering medium 9. As indicated in FIG. 1, the scattering medium 9 may, for example, be introduced into the container 2 as cooled liquid phase 9' by means of a metering unit 10 in the area of the inspection device 1. The liquid phase 9' may be liquid nitrogen, for example. As a result of evaporation of the liquid phase 9' at room temperature and accompanying cooling of the air 11 in the interior of the containers 2, a mist forms in conjunction with the air moisture prevailing in the interior of the containers 2, which serves as a scattering medium 9.

The scattering medium 9 is preferably a liquid and heavier than the air 11, thereby simplifying the handling of the container 2 in which the scattering medium 9 is admitted. For example, the scattering medium 9 could then also continue to remain in the container 2 for a subsequent treatment step. The scattering medium 9 can also be produced by other cooled liquid phases, such as carbon dioxide, for example, and/or it can be provided in particular also in the form of pressure-release mist, as is formed, for example, during demolding of blown plastic containers. For improved handling of non-settling liquids, the containers' 2 could be temporarily sealed.

It would be equally conceivable to supplement a pressure-release mist already present in the containers 2 in the area of the inspection device 1, for example, by liquid phase 9' or another fluid in order to form the scattering medium 9. Fluids suitable for forming the scattering medium 9 are gases, vapors, mist and/or smoke. It is crucial that the scattering medium 9 allow for sufficient diffusion of radiation in terms of the bright field irradiation. Particularly suited in this regard is refraction on small droplets, such as in mists and the like, for example. Scattering media 9 in the form of inflatable scattering balloons in the interior of the container 2 would also be conceivable, depending on hygienic requirements.

As is apparent from the first inspection unit 1a for bottom inspection, the scattering medium 9 makes it possible to illuminate the wall section 2a to be inspected even behind structures 2d, such as recessed grips, which in conventionally directional illumination from above would shade the wall section being examined. In contrast, the scattering medium 9 contacting the wall area 2a to be inspected enables the radiation to be homogenously diffused even directly behind the wall area 2a to be inspected. In this way a diffuse bright field is provided which in particular makes it possible, as is also indicated in the area of the second inspection unit 1b, to locate the radiation sources 7a to 7c outside the image region of the cameras 5a to 5c. In other words, the radiation sources 7a to 7c do not, from the perspective of the cameras 5a to 5c themselves, have to be located behind the wall section 2a to 2c being imaged.

This is made possible, for example, by arranging the cameras 5b, 5c indicated in FIG. 2 on both sides of the transporter 3 in order to image the opposing side wall areas 2b, 2c of the containers 2 at one common inspection position. The cameras 5b, 5c are thus able to image the opposing side wall areas 2b, 2c of the container 2 without changing the rotational position of the container 2 and/or essentially simultaneously. In addition, a circumferentially complete imaging of the containers 2 in the area of the second inspection unit 1b is possible in combination with a mirror cabinet (not shown) in the area of the cameras 5b, 5c, without having to rotate the containers 2 between individual exposures of the cameras 5b, 5c. The transporter 3 comprises, for example, suitably arranged belts, holders and the like to prevent the irradiation and imaging beam paths from being obstructed.

Figure 3:
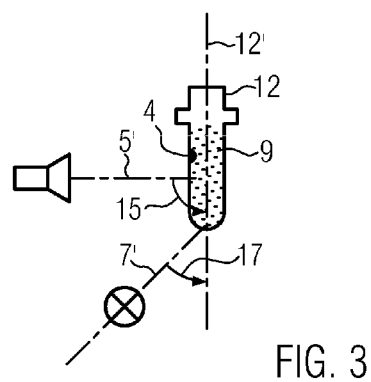
FIG. 3 is a schematic front view of an assembly according to the invention of a radiation source and a camera.

The same advantages may also be achieved in the inspection of preforms 12 for plastic bottles to be blow-molded, as is indicated schematically in FIG. 3. The scattering medium 9 could be introduced into the preform 12 in gaseous form, for example, by means of a rinser.

As is also indicated schematically in FIG. 3, the scattering medium 9 makes it possible to orthogonally align the main radiation direction 7' of the radiation sources 7a to 7c relative to the viewing direction 5' of the cameras 5a to 5c. Such an orthogonal alignment of the radiation sources and cameras is particularly advantageous, for example, for inspecting the side wall of the containers 2. An oblique alignment of the main radiation direction 7' relative to the viewing direction 5' is also conceivable, however. This is indicated schematically in FIG. 3 with the aid of angles 15, 17, which form the viewing direction 5' and the main radiation direction 7', in each case with the main axis 2' of the containers 2. The angles 17, 17 differ from one another preferably by 45 to 135 degrees.

Nonetheless, the radiation sources and cameras could also be arranged opposite one another relative to the scattering medium 9, in the case of the first inspection unit 1a, for example, above the containers 2 to be inspected. In such case, the angles 15, 17 would by definition differ by 180 degrees. Thus, the scattering medium 9 allows for a number of radiation variations through different wall areas of the containers 2 or the preforms 12 and/or through the mouths thereof. As a result, the inspection units according to the invention may be very compact in design. Likewise, differently shaped containers 2, for example, those with complex container shapes, may be uniformly illuminated and imaged in the bright field.

The inspection units 1a, 1b depicted are merely exemplary. The following areas of the containers 2 may also be inspected with the aid of the scattering medium 9: sealing surfaces, the interior surface of the side wall, closure threads, as well as lateral areas of the container mouth. With this configuration, it is possible to detect in a known manner as contrast differences foreign particles 4 in front of the bright field produced by the scattering medium 9, such as film residue and glass splinters, as well as damage, such as chipping and the like.

The scattering medium 9 could, for example, be swirled in the interior of the containers 2 in order to produce a uniform distribution of the scattering medium 9 in the containers 2 or preforms 12. The scattering medium 9 could, for example, continue to remain in the containers 2 for a subsequent treatment step. Nitrogen mist, for example, would be suitable, which in a subsequent filling process is left behind on the liquid poured in (not shown) making a hygienic cold filling possible. Likewise, the scattering medium 9 could also have a sterilizing effect. As a result, scattering medium 9 could be used for additional treatment steps for the containers 2 or preforms 12. The scattering medium 9 is preferably a fluid which can be introduced, for example, by injecting it into the containers 2 or preforms 12 within at most 100 milliseconds, preferably within at most 10 milliseconds. The scattering medium 9 can also be introduced in gaseous phase under pressure.

Because the scattering medium 9 reaches to the interior wall of each of the wall areas 2a to 2c to be inspected, it is possible to illuminate by means of light scattering wall areas that are not accessible to illumination due to light refraction on the surfaces of the container.

It would also be conceivable to use the scattering medium 9 to measure the wall thickness of the containers 2. In such case, it would be sufficient to irradiate the scattering medium 9 at an appropriate radiation wave length and to detect the radiation intensity after the measuring radiation has passed once through the container wall.

An irradiation of the scattering medium 9 according to the invention would also be conceivable during a visual inspection of the fill level of the containers 2. In such case, liquid nitrogen, for example, could be introduced into the headspace of the containers 2 and illuminated. In such case, the nitrogen mist and foam make it possible to differentiate the filled product.

The device 1 according to the present disclosure may be operated, for example, as follows:

The scattering medium 9 is provided in the interior of the containers 2 or preforms 12, for example, by means of a pressure-release mist remaining in the containers 2 after they have been demolded, or by introducing the scattering medium 9, in gaseous phase, for example, into the preforms 12 immediately prior to inspection. The scattering medium 9 is distributed in the containers 2 or in the preforms 12 prior to inspection in such a way that the scattering medium 9 is in contact with the latter in the area of the respective wall areas 2a to 2c to be inspected. The scattering medium 9 is then irradiated such that in the wall areas 2a to 2c to be imaged a virtual radiation source is produced which serves as a bright field for imaging the wall areas 2a to 2c. The wall areas 2a to 2c to be inspected are then imaged in transmitted light during the aforementioned bright field illumination. The imaged wall areas may be evaluated with the aid of known image evaluation processes. For example, local differences in brightness in the bright field produced can be compensated by a suitable calibration and/or averaging of individual exposures.

The scattering means 9 may continue to remain in the containers 2 to be inspected or in the preforms 12, both for inspecting different wall areas 2a to 2c, for detecting various damage and/or foreign particles, as well as for a subsequent treatment step. Thus, the scattering medium 9 may be used in different inspection units 1a, 1b as virtual radiation sources for illuminating the bright field of wall areas 2a to 2c to be inspected.

The radiation sources 7a to 7c may be more compactly designed and with greater design freedom as compared to the prior art. In particular, it is possible to arrange the radiation sources in such a way that a circumferentially complete side wall inspection is made possible at one single inspection position. In contrast, the prior art requires two inspection positions having separate illumination and imaging systems along a transport. While pressure-release mists in the containers 2 to be inspected have represented a disruptive factor in conventional inspection methods, the method according to the invention allows for an advantageous use of pressure-release mists and makes it unnecessary to optionally introduce additional scattering media 9 into the containers 2 or preforms to be inspected.

The variations of the invention described may be combined in any technically feasible manner.

The invention claimed is:

1. A method for inspecting containers or preforms, comprising:
   a) providing a scattering medium in an interior of the containers or preforms;
   b) irradiating the scattering medium in such a way that the scattering medium forms a bright field behind a wall area of the container or preform to be imaged; and
   c) imaging the wall area, wherein at least when imaging the wall area, the scattering medium is present in a gaseous form.

2. The method according to claim 1, wherein the scattering medium is heavier than air.

3. The method according to claim 1, wherein the scattering medium is supplied cooled in liquid phase.

4. The method according to claim 1, wherein the scattering medium comprises a pressure-release mist.

5. The method according to claim 1, wherein the scattering medium in step c) is in contact with the wall area.

6. The method according to claim 1, wherein the scattering medium has a sterilizing effect.

7. The method according to claim 1, wherein the wall area to be imaged is a bottom of the containers or preforms and the scattering medium is irradiated through at least one of a side wall or a mouth of the containers or preforms.

8. The method according to claim 1, wherein the wall area to be imaged is a side wall of the containers or preforms and the scattering medium is irradiated from at least one of above or below the containers or preforms.

9. The method according to claim 1, wherein the spatial distribution of the scattering medium in the area of the wall section to be imaged is symmetrical relative to the main axis of the containers.

10. The method according to claim 1, further comprising moving the containers or preforms in steps a) to c) along a conveyor line.

11. The method according to claim 10, wherein the scattering medium is irradiated successively from at least two different main radiation directions, in order to provide at least two bright fields along the conveyor line for the inspection of different wall areas.

12. A device for inspecting containers or preforms, comprising:
    at least one camera for imaging a wall area of the containers or preforms to be inspected;
    a source for at least one of providing or distributing a scattering medium in a gaseous medium form in the interior of the containers or preforms; and
    at least one radiation source for irradiating the scattering medium in such a way that the irradiated scattering medium forms a bright field during imaging of the wall area.

13. The device according to claim 12, wherein the main radiation direction of the radiation source and the viewing direction of the camera differ from one another by 45° to 135° relative to the main axis of the containers or preforms.

14. The device according to claim 12, wherein two cameras are provided opposite one another on both sides of a transport line for the containers or preforms in the area of the radiation source, in such a way that the cameras are, at least one of at a common inspection position relative to the transport line simultaneously, able to image the irradiated containers or preforms.

15. The method according to claim 1, wherein the scattering medium is present as at least one of steam, mist, or smoke.

16. The method according to claim 3, wherein in supplying the scattering medium cooled in liquid phase, the scattering medium is supplied in the form of liquid nitrogen.

17. The method according to claim 4, wherein the pressure-release mist results from a pressure-release during the manufacturing of the containers to be inspected.

18. The method according to claim 8, wherein the scattering medium is irradiated through at least one of a month or a bottom of the containers or preforms.

* * * * *